United States Patent
Dou

(10) Patent No.: US 10,463,378 B2
(45) Date of Patent: Nov. 5, 2019

(54) BILATERAL FEMORAL ARTERY HEMOSTASIS DEVICE BY COMPRESSION

(71) Applicant: Zhigang Dou, Zhengzhou (CN)

(72) Inventor: Zhigang Dou, Zhengzhou (CN)

( * ) Notice: Subject to any disclaimer, the term of this patent is extended or adjusted under 35 U.S.C. 154(b) by 118 days.

(21) Appl. No.: 15/462,890

(22) Filed: Mar. 19, 2017

(65) Prior Publication Data

US 2018/0250016 A1 Sep. 6, 2018

Related U.S. Application Data

(63) Continuation of application No. PCT/CN2015/079465, filed on Feb. 7, 2015, and a
(Continued)

(30) Foreign Application Priority Data

Jan. 30, 2015 (CN) ..................... 2015 2 0066832 U
Feb. 7, 2015 (CN) ......................... 2015 1 0065851

(51) Int. Cl.
*A61B 17/132* (2006.01)
*A61B 17/122* (2006.01)
(Continued)

(52) U.S. Cl.
CPC .......... *A61B 17/132* (2013.01); *A61B 17/122* (2013.01); *A61B 2017/0042* (2013.01); *A61B 2017/12004* (2013.01)

(58) Field of Classification Search
CPC ... A61B 17/12; A61B 17/132; A61B 17/1322; A61B 17/1325; A61B 17/1327;
(Continued)

(56) References Cited

U.S. PATENT DOCUMENTS

| 5,514,155 A * | 5/1996 | Daneshvar ......... A61B 17/1325 128/118.1 |
| 2007/0005090 A1* | 1/2007 | Whitmore, III ... A61B 17/0057 606/191 |

(Continued)

FOREIGN PATENT DOCUMENTS

CN             204445999 U      7/2015

*Primary Examiner* — Kathleen S Holwerda
*Assistant Examiner* — Kankindi Rwego
(74) *Attorney, Agent, or Firm* — Wayne & Ken, LLC; Tony Hom

(57) ABSTRACT

A bilateral femoral artery hemostasis device by compression comprises a first pressing plate, a second pressing plate and a bellyband; the bellyband comprises more than one fixing belt and more than one elastic compression hemostasis belt, the second pressing plate is located above the first pressing plate, the second pressing plate is more than one; the first pressing plate comprises a compression plate located at a bottom of the first pressing plate and a top plate located at an upper part of the first pressing plate; a first pressing plate supporting leg is vertically arranged on an upper side surface of the top plate, and a space for the fixing belt to pass through is provided between the first compressing plate supporting legs. The hemostasis device is simple to operate, and only one medical staff member can complete all operations, thereby reducing the work intensity of the medical staff.

5 Claims, 5 Drawing Sheets

Related U.S. Application Data continuation of application No. PCT/CN2015/096613, filed on Jan. 30, 2015.

(51) Int. Cl.
    *A61B 17/00*     (2006.01)
    *A61B 17/12*     (2006.01)

(58) Field of Classification Search
    CPC ...... A61B 2017/12004; A61H 2205/00; A61H 2205/08; A61H 2205/081; A61H 2205/083; A61H 2205/085; A61H 2205/086; A61H 2205/10; A61H 2205/108
    USPC .......................................................... 606/280
    See application file for complete search history.

(56) References Cited

U.S. PATENT DOCUMENTS

2013/0289614 A1* 10/2013 Cully ................. A61B 17/1322
    606/203
2013/0296921 A1* 11/2013 Saunders ........... A61B 17/1325
    606/203

* cited by examiner

BILATERAL FEMORAL ARTERY HEMOSTASIS DEVICE BY COMPRESSION

TECHNICAL FIELD

The present invention relates to the field of medical devices, and more specifically, to a bilateral femoral artery hemostasis device by compression.

BACKGROUND OF THE PRESENT INVENTION

After the intervention technology of femoral artery is completed, compression haemostasis method is generally adopted. The advantages are vascular structure is not destroyed, the objects filled with gel or collagen are not needed to be stitched, hospitalization time of patients is shortened, and artery blood vessel can be puncture used repeatedly for many times in short time. However, the disadvantages are working strength of medical personnel is increased, and immobilization on bed of patients for 24 h affects body recovery of patients after operation severely. Besides, traditional bandage of existing hemostasis device needs complicated binding process, unprofessional personnel is unable to operate, and patients are unable to move lightly, otherwise the hemostasis device will be displaced.

SUMMARY OF THE PRESENT INVENTION

The purpose of the present invention is to provide a bilateral femoral artery hemostasis device by compression which can stably compress the bleeding point and reduce the operation difficulty. The device can be easily adjusted, so as to be more comfortable for patients. And medical cost is saved.

The technical scheme of the present invention is as follows:

A bilateral femoral artery hemostasis device by compression, comprising a first pressing plate, one or more second pressing plates and a trouser-type bellyband; the trouser-type bellyband comprises more than one puncture-point compression fixing belt and more than one elastic puncture-point compression hemostasis belt, the second pressing plates are located above the first pressing plate the first pressing plate comprises a compression plate located at a bottom of the first pressing plate and a top plate located at an upper part of the first pressing plate; a plurality of first pressing plate supporting legs are vertically arranged on an upper side surface of the top plate, and a first space for the puncture-point compression fixing belt of the trouser-type bellyband to pass through is provided between the first pressing plate supporting legs; a first clamping mechanism is provided between the first pressing plate supporting legs and the second pressing plate, and the first pressing plate supporting legs are clamped with one of the second pressing plates by the first clamping mechanism; an anti-slipping bulge is provided on the upper side surface of the top plate for preventing the puncture-point compression fixing belt and the puncture-point compression hemostasis belt slipping; and a hemispheric bulge is provided at a bottom side of the compression plate.

Each of the second pressing plates comprises a second pressing plate body and a plurality of second pressing plate supporting legs connected on an upper side of the second pressing plate body, and a second space for the puncture-point compression hemostasis belt of the trouser-type bellyband to pass through is provided between the second pressing plate supporting legs.

The second pressing plates are stacked, and a second clamping mechanism is provided between the second pressing plate supporting legs of one of the second pressing plates and the adjacent second pressing plate body.

The second clamping mechanism comprises a second clamping bulge and a clamping slot, the second clamping bulge or the clamping slot is provided on each of the second pressing plate supporting legs, and the clamping slot or the second clamping bulge are correspondingly provided on the second pressing plate body.

The first clamping mechanism comprises the first clamping bulge and the clamping slot fitted with the first clamping bulge, the first clamping bulge is provided on a top of each of the first pressing plate supporting legs or a bottom of the second pressing plate, and the clamping slot is correspondingly provided on the bottom of the second pressing plate or the top of each of the first pressing plate supporting legs.

Four first pressing plate supporting legs are vertically arranged on a periphery of the upper side of the top plate.

The number of the anti-slipping bulge is four, and four anti-slipping bulges are uniformly distributed on the upper side of the top plate.

The trouser-type bellyband comprises an annular abdomen fixing belt portion and two leg fixing belt portions, and the puncture-point compression fixing belt and the puncture-point compression hemostasis belt are obliquely connected between the abdomen fixing belt portion and the two leg fixing belt portions.

The abdomen fixing belt portion is provided with an abdomen sticky buckle, and the leg fixing belt portion is provided with a leg sticky buckle.

The abdomen fixing belt portion comprises a buttock portion and a crotch portion located outside, the puncture-point compression fixing belt at one side and one end of the puncture-point compression hemostasis belt are fixedly connected to a back side of the leg fixing belt portion, and the puncture-point compression fixing belt and the other end of the puncture-point compression hemostasis belt are connected on the buttock portion or the crotch portion.

The present invention comprises a trouser-type bellyband, two pressing plates, the first pressing plate is provided with four bulges, and the second pressing plate is provided with four grooves, a semicircle is arranged under the first pressing plate to compress the hemorrhagic spot. The first pressing plate is fixed with the fixing belt, after the bleeding point is compressed with the first pressing plate. The first pressing plate is then compressed by the second pressing plates, and then the second pressing plates are fixed with the compression belt. The present invention is of simple structure, after interventional operation is completed, the hemostasis device is simple to operate, time and energy are saved, and working strength of medical personnel is reduced.

The trouser-type of the present invention is disposable, two sticky buckles are added respectively on buttock and waist on both side of the trouser-type bellyband, and two belts are added respectively on left and right thighs at back side of the buttock. Two belts are provided with the sticky buckle, one belt is compression hemostasis belt, which is made of stretch material, and the other is the fixing belt for completing the compression hemostasis after femoral artery double-side puncture simultaneously. The bilateral femoral artery hemostasis device by compression adopts stacked pressing plate to fit different obese patients, the base of the bilateral femoral artery hemostasis device by compression is hemisphere, and the center point is oval, so that hemorrhagic spot of blood vessel can be captured, and the hemorrhagic spot can reach the greatest pressure, the base and the first pressing plate are connected by a column, the first pressing plate is double hammer-shaped, four bulges are provided at the middle bottom for increasing the friction force between the pressing plate and the compression belt, so that the fixed point is stabilized, and two column bulges are provided respectively above the double hammer. The second pressing plate is basically similar to the first pressing plate, and the difference is that two grooves are arranged under hammer of the second pressing plate for connecting the first pressing plate.

The upper end of oblique sticky buckle is connected to the crotch or buttock at one side or two sides.

Advantages: 1. The device has the advantages that the operation is simple, the whole operation can be completed only through one medical personnel, the existing method of manually pressing for 30 minutes is replaced, meanwhile, the traditional complicated bandage type fixing and compression hemostasis method can be replaced, and the work intensity of the medical personnel is greatly reduced.

2. The product is of compact structure, fixed firmly, exact compression point and not easy to move. Light activity of patients on bed will not affect the position and pressure of compression point, which solves discomfort of patients when they are unable to move during immobilization time, and can solve immobilization time of patients.

DETAILED DESCRIPTION OF PREFERRED EMBODIMENTS

Figure 1:
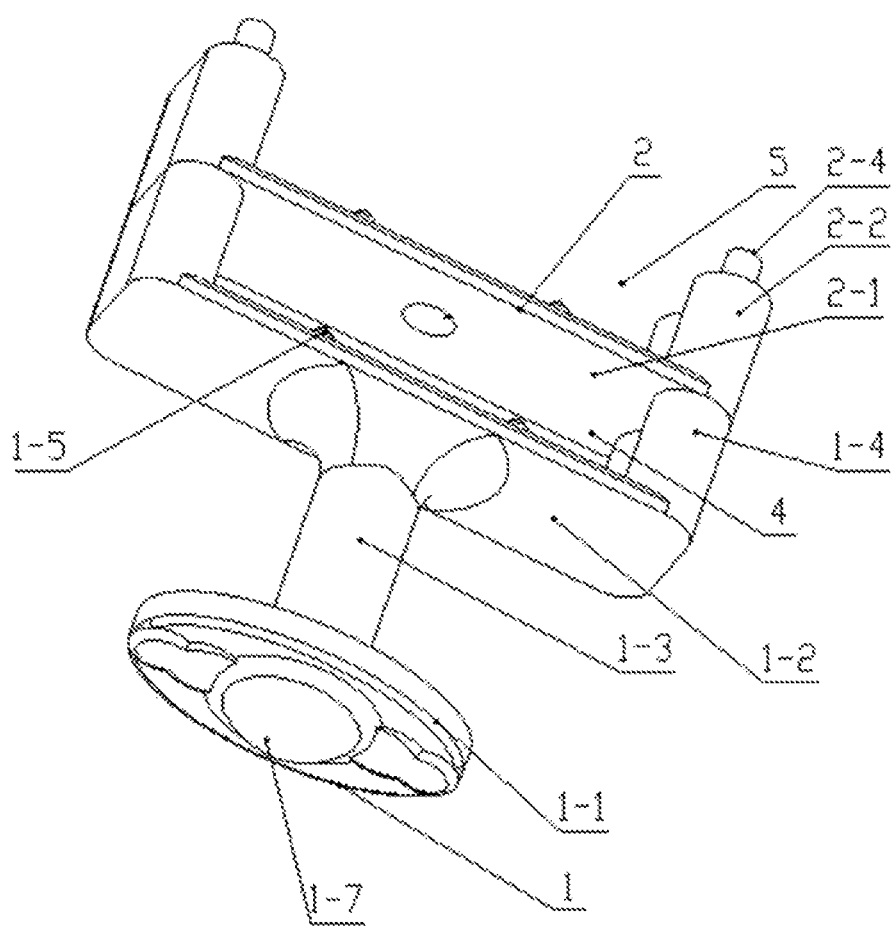
FIG. 1 is a structure diagram of the present invention.
Figure 2:
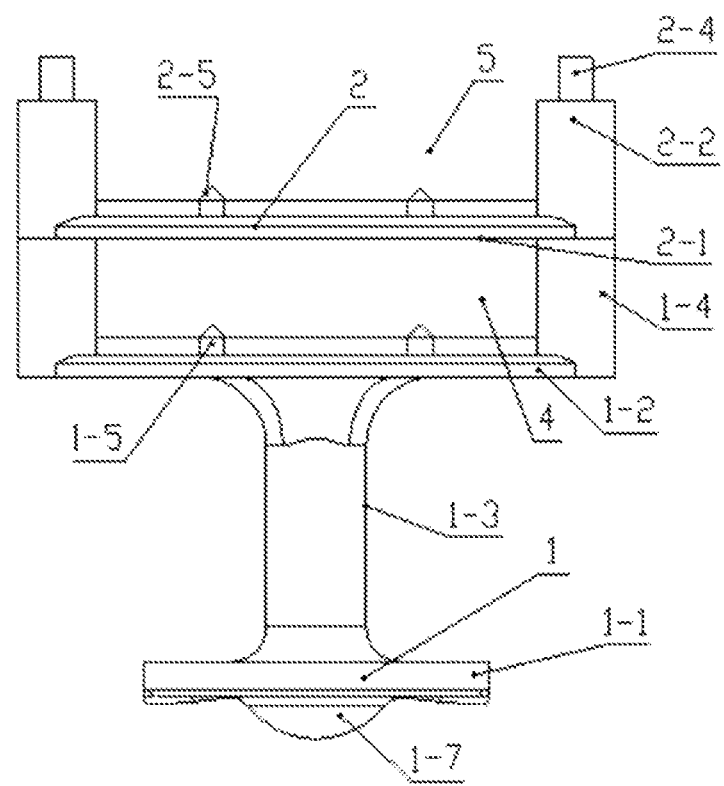
FIG. 2 is a front view of FIG. 1.
Figure 5:
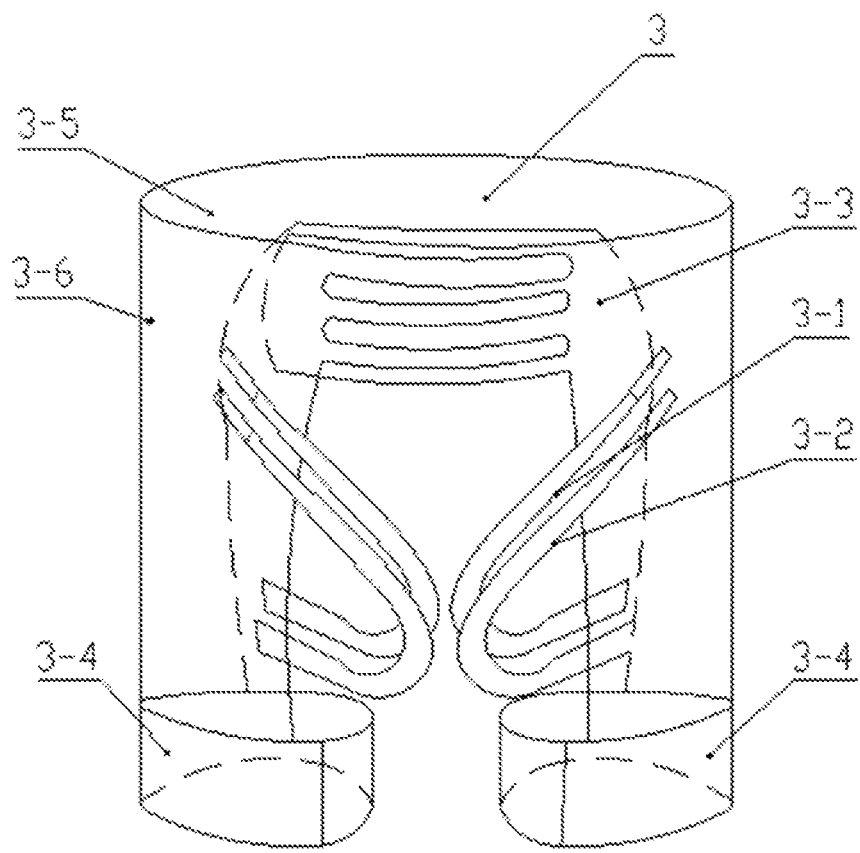
FIG. 5 is a structure diagram of a trouser-type bellyband.

As shown in FIG. 1, FIG. 2 and FIG. 5, the present invention comprises a first pressing plate 1, a plurality of second pressing plates 2 and a trouser-type bellyband 3, the second pressing plates 2 are located above the first pressing plate 1, the quantity is based on actual need, multiple second pressing plates should be stacked together for use of the fatter.

Figure 3:
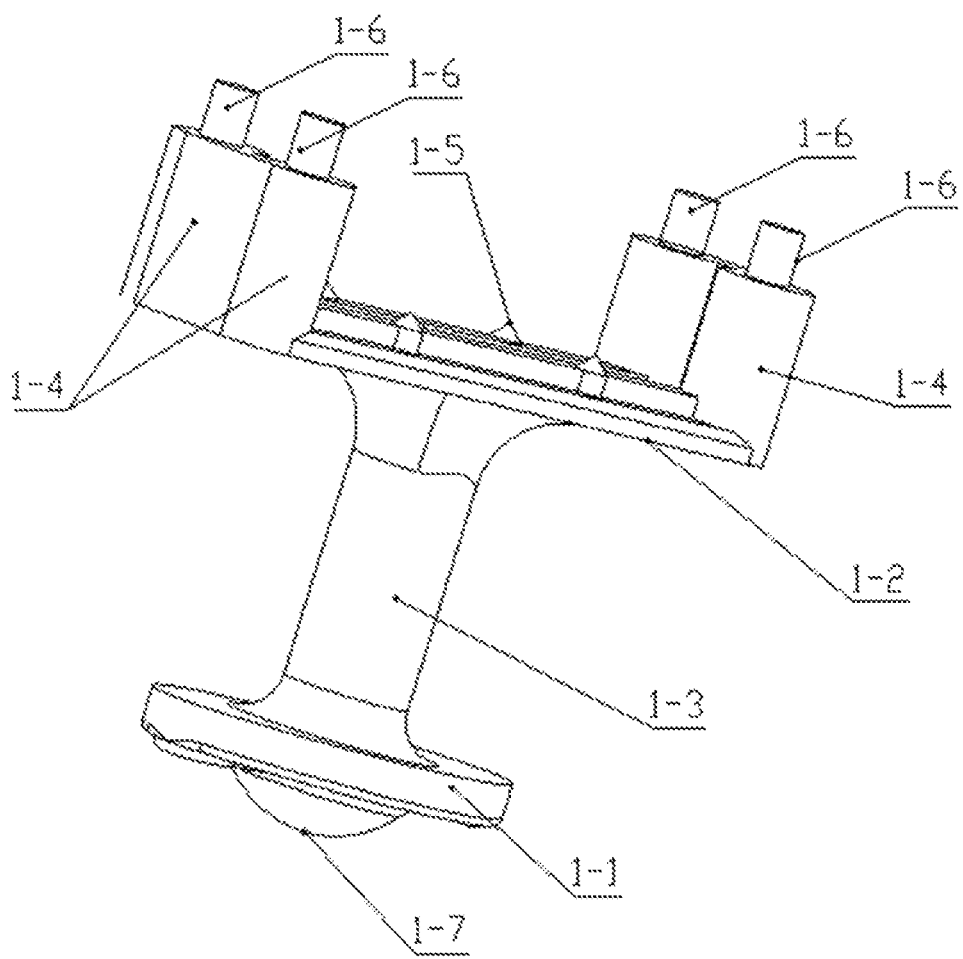
FIG. 3 is a structure diagram of a first pressing plate.

As shown in FIG. 3, the first pressing plate 1 comprises a compression plate 1-1 located at the bottom of the first pressing plate 1 and a top plate 1-2 located on the upper part of the first pressing plate 1. The first pressing plate 1-1 is ellipse, the top plate 1-2 is rectangle, and a compression column 1-3 is provided between the compression plate 1-1 and the top plate 1-2. A plurality of first pressing plate supporting legs 1-4 are vertically arranged on a side surface of the top plate 1-2, and a first space 4 for the fixing belt of the trouser-type bellyband to pass through is provided between the first pressing plate supporting legs 1-4.

A first clamping mechanism is provided between the first pressing plate supporting legs 1-4 and one of the second pressing plates 2, and the first pressing plate supporting legs 1-4 are clamped with one of the second pressing plates 2 by the first clamping mechanism;

The first clamping mechanism comprises the first clamping bulge 1-6 and a clamping slot 2-3 fitted with the first clamping bulge 1-6, the first clamping bulge 1-6 is provided on a top of each of the first pressing plate supporting legs 1-4, and the clamping slot 2-3 is correspondingly provided on the bottom of one of the second pressing plates 2.

Four first pressing plate supporting legs 1-4 are vertically arranged on a periphery of the upper side of the top plate 1-2. The purpose can also be realized by providing one wider supporting leg on both sides of the top plate 1-2 respectively.

Four anti-slipping bulges 1-5 are uniformly distributed on an upper side of the top plate 1-2 for preventing the compression fixing belt slipping.

The anti-slipping bulge 1-5 is located at a bottom of the first space 4 for the puncture-point compression fixing belt to pass through, a hemispheric bulge 1-7 is provided on the bottom of the compression plate 1-1 for compressing the hemorrhage spot.

Figure 4:
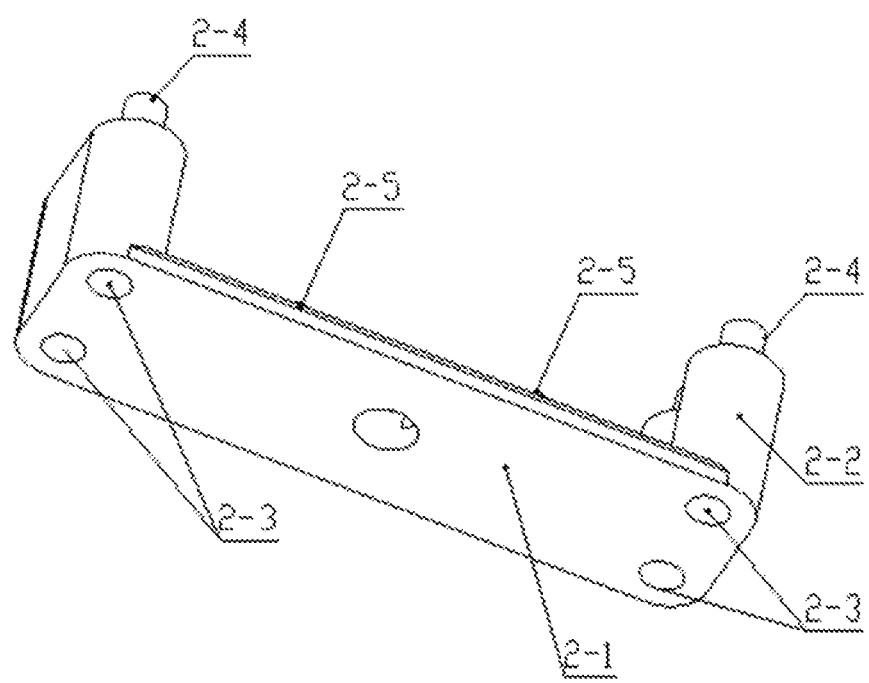
FIG. 4 is a structure diagram of a second pressing plate.

As shown in FIG. 4, each of the second pressing plates 2 comprises a second pressing plate body 2-1 and a plurality of second pressing plate supporting legs 2-2 connected on an upper side of the second pressing plate body 2-1, the second pressing plate legs 2-2 are more than two, and a second space 5 for the compression hemostasis belt of the trouser-type bellyband to pass through is provided between the second pressing plate supporting legs. Four anti-slipping bulges 2-5 are also provided on the upper side of the second pressing plate body 2-1 for preventing the elastic compression belt slipping.

The second pressing plates are stacked, and a second clamping mechanism is provided between each of the second pressing plate supporting legs 2-2 of the second pressing plates 2 and the adjacent second pressing plate body 2-1. The second clamping mechanism comprises a second clamping bulge 2-4 and the clamping slot 2-3, the second clamping bulge is provided on each of the second pressing plate supporting leg 2-2, and the clamping slot 2-3 is correspondingly provided on the second pressing plate body 2-1. A plurality of the second pressing plates 2 can be stacked based on need, the second space 5 for the compression hemostasis belt to pass through is provided at the top of the second pressing plates 2, the compression hemostasis belt is pulled to provide pressure on the second pressing plate 2, so that the second pressing plate 2 compresses the first pressing plate 1 downwards.

As shown in FIG. 5, the trouser-type bellyband 3 comprises a puncture-point compression fixing belt 3-1, an elastic puncture-point compression belt 3-2, and a sticky buckle. the trouser-type bellyband comprises an annular abdomen fixing belt portion 3-3 and two leg fixing belt portions 3-4, and the abdomen fixing belt portion 3-3 and two leg fixing belt portions 3-4 are integrally connected. The abdomen fixing belt portion 3-3 is provided with an abdomen sticky buckle, and the leg fixing belt portion 3-4 is provided with a leg sticky buckle.

The abdomen fixing belt portion 3-3 comprises a buttock portion 3-5 and a crotch portion 3-6 located outside, and the sticky buckle is provided.

The puncture-point compression fixing belt 3-1 and the elastic puncture-point compression belt 3-2 are obliquely connected between the abdomen fixing belt portion 3-3 and two leg fixing belt portions 3-4. Specifically, lower ends of the puncture-point compression fixing belt 3-1 and the elastic puncture-point compression belt 3-2 are connected at back side of the leg fixing belt portion 3-4, and upper ends of the puncture-point compression fixing belt 3-1 and the elastic puncture-point compression belt 3-2 are connected at the buttock portion 3-5 and the crotch portion 3-6.

Use Method of the Product:

1. The trouser-type bellyband is laid on an operating bed before operation, wherein the patient lies on the trouser-type bellyband, and the buttock of the patient is located in the center of the trouser-type bellyband.

2. After the interventional operation is completed, the two leg fixing belt portions are fixed, and abdomen fixing belt is then fixed. After the pulse of arteria dorsalis pedis is confirmed by the operator, arteriovenous sheath is withdrawn from 2 cm, and the arteriovenous puncture point is conformed and covered with sterile gauze. The compression device is then taken out, and the compression point is found. The puncture-point compression fixing belt passes through the first pressing plate and fixed on the sticky buckle at back side of the buttock with pressure, the arteriovenous sheath is removed, and the second pressing plate is fastened on the first pressing plate, and the elastic puncture-point compression belt passes through the second pressing plate and is fixed on the sticky buckle at back side of the buttock with pressure, the pulse of arteria dorsalis pedis is checked, and the pulse should be weakened but not lost.

3. After the puncture point is compressed for 30 min, the puncture point is pressed with left hand, and the compression device is removed with right hand, bleeding point is pressed with medical gauze, the puncture-point compression fixing belt is pressed on top of the medical gauze, and and then fixed on the sticky buckle at back side of the buttock. The elastic puncture-point compression belt is then pressed and fixed on top of the puncture-point compression fixing belt with the sticky buckle at back side of the buttock. The operator performs femoral artery compression hemostasis on the other side according to above-mentioned method, and double-side femoral artery compression hemostasis is then completed.

What is claimed is:

1. A bilateral compression hemostasis device of femoral artery, wherein the hemostasis device comprises a first pressing plate, one or more second pressing plates and a trouser-type bellyband; wherein
    the trouser-type bellyband comprises more than one fixing belt and more than one elastic compression hemostasis belt;
    the second pressing plates are located above the first pressing plate;
    the first pressing plate comprises a compression plate located at a bottom of the first pressing plate and a top plate located at an upper part of the first pressing plate;
    a compression column is provided between the compression plate and the top plate; one end of the compression column is connected to the compression plate, the other end of the compression column is connected to the top plate;
    a plurality of first pressing plate supporting legs are vertically arranged on an upper side surface of the top plate, and a first space for the fixing belts of the trouser-type bellyband to pass through is provided between the plurality of first pressing plate supporting legs;
    a first clamping mechanism is provided between the plurality of first pressing plate supporting legs and one of the one or more second pressing plates, and the plurality of first pressing plate supporting legs are clamped with one of the one or more second pressing plates by the first clamping mechanism;
    the first clamping mechanism comprises a plurality of first clamping bulges and a plurality of clamping slots fitted with the plurality of first clamping bulges; the plurality of first clamping bulges are provided on tops of the plurality of first pressing plate supporting legs or a bottom of the one of the one or more second pressing plates;
    and the plurality of clamping slots are correspondingly provided on the bottom of the one of the one or more second pressing plates or the tops of the plurality of first pressing plate supporting legs;
    a first anti-slipping bulge is provided on the upper side surface of the top plate for preventing a slipping of the fixing belts; and
    a hemispheric bulge or a semi-elliptic bulge is provided at a bottom side of the compression plate;
    each of the second pressing plates comprises a second pressing plate body and a plurality of second pressing plate supporting legs connected on an upper side of the second pressing plate body, and a second space for the elastic compression hemostasis belts of the trouser-type bellyband to pass through is provided between the plurality of second pressing plate supporting legs; the second space is arranged over the first space in a vertical direction; the plurality of second pressing plate supporting legs are respectively coaxially connected to the plurality of first pressing plate supporting legs;
    a second anti-slipping bulge is provided on an upper side surface of one of the second pressing plate body;
    the trouser-type bellyband comprises an annular abdomen fixing belt portion and two leg fixing belt portions, and the fixing belts and the elastic compression hemostasis belts are obliquely connected between the annular abdomen fixing belt portion and the two leg fixing belt portions.

2. The device of claim 1, wherein the second pressing plates are stacked, and a second clamping mechanism is provided between the plurality of second pressing plate supporting legs of one of the second pressing plates and an adjacent second pressing plate body;
    the second clamping mechanism comprises a plurality of second clamping bulges and a plurality of second clamping slots; the plurality of second clamping bulges are provided on tops of the plurality of second pressing plate supporting legs or a bottom of the adjacent second pressing plate body.

3. The device of claim 1, wherein the plurality of first pressing plate supporting legs are vertically arranged on a periphery of the upper side surface of the top plate.

4. The device of claim 1, wherein a number of the anti-slipping bulge is four, and the anti-slipping bulges are uniformly distributed on the upper side surface of the top plate.

5. The device of claim 1, wherein the abdomen fixing belt portion of the trouser-type bellyband comprises a buttock portion and a crotch portion located opposite the buttock portion, and wherein one end of each of the fixing belts and one end of each of the elastic compression hemostasis belts are fixedly connected to a back side of each of the leg fixing belt portions, and wherein the other end of each of the fixing belts and each of the elastic compression hemostasis belts are connected to one of the buttock portion and the crotch portion.

* * * * *